United States Patent [19]
Chang et al.

[11] Patent Number: 5,811,284
[45] Date of Patent: Sep. 22, 1998

[54] NUCLEIC ACIDS ENCODING KP43 PROTEIN AND ANTIGENIC FRAGMENTS THEREOF

[75] Inventors: Chiwen Chang, San Jose, Calif.; José Aramburu Beltrán, Fagina n.3, Irun-20300; Miguel López-Botet, Manuel del Valle n.5, pl-1G, Madrid-28043, both of Spain; Joseph H. Phillips, Jr., San Carlos; Lewis L. Lanier, Los Altos, both of Calif.

[73] Assignees: Schering Corporation, Kenilworth, N.J.; José Aramburu Beltrán, Irun; Miguel López-Botet, Madrid, both of Spain

[21] Appl. No.: 650,578

[22] Filed: May 20, 1996

Related U.S. Application Data

[63] Continuation of Ser. No. 175,339, Dec. 29, 1993, abandoned.

[51] Int. Cl.⁶ .............................. C12N 1/21; C12N 5/10; C12N 15/12
[52] U.S. Cl. ..................... 435/252.3; 435/320.1; 435/69.1; 435/325; 536/23.1; 536/23.5; 536/24.3; 536/24.31; 536/24.33
[58] Field of Search ............... 536/23.5, 23.1, 536/24.3, 24.31, 24.33; 530/350; 435/320.1, 252.3, 69.1, 325

[56] References Cited

PUBLICATIONS

Houchins et al. *J. Exp. Med.* 173;1017–1020 (Apr. 1991).
Bowie et al. Science 247:1306–1310, 1990.
Ngo et al. The Protein Folding Problem and tertiary Structure Prediction, Merz et al, eds, Birkhauser, Boston, 1994.
Reeck et al. Cell 50:667. 1987.
Lewin. Science 237:1570, 1987.
Jose Aramburu, et al., "A Novel Functional Cell Surface Dimer (Kp43) Expressed by Natural Killer Cells and T Cell Receptor–γ/δ T Lymphocytes: I. Inhibition of the IL–2 Dependent Proliferation by Anti–Kp43 Monoclonal Antibody," *J. Immunol.*, 144:3238–3247, Apr. 15, 1990.

Jose Aramburu, et. al., "A Novel Functional Cell Surface Dimer (Kp43) Expressed by Natural Killer Cells and T Cell Receptor–γ/δ T Lymphocytes: II. Modulation of Natural Killer Cytotoxicity by Anti–Kp43 Monoclonal Antibody," *J. Immunol.*, 147:714–721, Jul. 15, 1991.

Jose Aramburu, et al., "Stimulation of IL–2–Activated Natural Killer Cells Through the Kp43 Surface Antigen Up–Regulates TNF–α Production Involving the LFA–1 Integrin," *J. Immunol.*, 151:3420–3429, Oct. 1, 1993.

Maria A. Balboa, et al., "Phospholipase D Activation in Human Natural Killer Cells through the Kp43 and CD16 Surface Antigens Takes Place by Different Mechanisms. Involvement of the Phospholipase D Pathway in Tumor Necrosis Factor α Synthesis," *J. Exp. Med.*, 176:9–17, Jul.1 992.

Christine A. Biron, et al., "Severe Herpesvirus Infection in an Adolescent Without Natural Killer Cells," *N. Engl. J. Med.*, 320:1731–1735, Jun. 1989.

Kurt Drickamer, "Evolution of $Ca^{2+}$–dependant Animal Lectins," *Prog. Nuc. Acids Res.*, 45:207–232, 1993.

Kazuo Oshimi, "Granular Lymphocyte Proliferative Disorders: Report of 12 Cases and Review of Literature," *Leukemia*, 2:617–627, Oct. 1988.

Gonzalo Rubio, et al., "A Novel Functional Cell Surface Dimer (kp43) Serves as Accessory Molecule fro the Activation of a Subset of Human γ/δ T Cells," *J. Immunol.*, 151:1312–1321, Aug. 1, 1993.

Wayne M. Yokoyama, "The Ly–49 and NKR–P1 Gene Families Encoding Lectin–Like Receptors on Natural Killer Cells: The NK Gene Complex," *Ann. Rev. Immunol.*, 11:613–635, 1993.

*Primary Examiner*—Elizabeth C. Kemmerer
*Attorney, Agent, or Firm*—Edwin P. Ching

[57] ABSTRACT

The invention provides nucleic acids and polypeptides encoding an NK cell surface antigen from a mammal, as well as antibodies that specifically bind the NK cell surface antigen. Methods of using the nucleic acids, polypeptides, and antibodies are provided, including diagnostic kits comprising one or more of these reagents.

15 Claims, No Drawings

NUCLEIC ACIDS ENCODING KP43 PROTEIN AND ANTIGENIC FRAGMENTS THEREOF

This application is a continuation of commonly assigned U.S. Ser. No. 08/175,339, filed Dec. 29, 1993, now abandoned.

FIELD OF THE INVENTION

The present invention relates to compositions related to proteins which function in controlling physiology, development, and differentiation of mammalian cells, e.g., cells of a mammalian immune system. In particular, it provides proteins and mimetics which regulate cellular physiology, development, differentiation, or function of various cell types, including hematopoietic cells, and particularly natural killer (NK) and T cells.

BACKGROUND OF THE INVENTION

The immune system of vertebrates consists of a number of organs and several different cell types. Two major cell types include the myeloid and lymphoid lineages. Among the lymphoid cell lineage are B cells, which were originally characterized as differentiating in fetal liver or adult bone marrow; T cells, which were originally characterized as differentiating in the thymus; and natural killer (NK) cells. See, e.g., Paul (ed.) (1993) *Fundamental Immunology* (3d ed.) Raven Press, New York. NK cells are phenotypically heterogeneous populations of large granular lymphocytes which display non-Major Histocompatibility Complex (MHC)-restricted cytolytic activity. These cells are characterized, in part, by their expression of non-lineage specific surface antigens, particularly the FcRIII (CD16) and NKH1 (CD56) markers. See, e.g., Ortaldo, et al. (1984) *Ann. Rev. Immunol.* 2:359–394; and Lanier, et al. (1986) *J. Immunol.* 136:4480–4486.

Soluble proteins, e.g., cytokines, and cell surface antigens, e.g., CD markers, play critical roles in regulating cellular interactions important in development of an immune response or in cellular differentiation. These cytokines and cell markers mediate cellular activities in many ways. They have been shown, e.g., to modulate proliferation, growth, and differentiation of hematopoietic stem cells into the vast number of cell types responsible for an immune response. In particular, interleukin-2 (IL-2) induces proliferation and cytotoxic activity of NK cells.

However, the cellular molecules which regulate differentiation and maturation of these cells are still incompletely identified. Moreover, the roles and mechanisms of action of signaling molecules which induce, sustain, or modulate the physiological, developmental, or proliferative states of these cells, particularly NK cells, is poorly understood. The proliferative and cytotoxic functions of NK cells are particularly important. Clearly, the immune system and its response to various stresses have relevance to medicine, e.g., infectious diseases, cancer related responses and treatment, allergic, autoimmune, and transplantation rejection responses. See, e.g., Thorn, et al. *Harrison's Principles of Internal Medicine* McGraw/Hill, New York.

Medical science relies, in large degree, to appropriate initiation or suppression of immune responses to effect cures for insufficient or improper physiological responses. However, lack of understanding of how the immune system is regulated or differentiates has blocked the ability to advantageously modulate normal or abnormal defensive mechanisms to biological challenges. Medical conditions characterized by abnormal or inappropriate regulation of proliferation or activation of relevant cells, e.g., NK cells, thus remain unmanageable. NK cells are particularly important in eliminating tumor, virus infected, and other specific target cells. The discovery and characterization of specific cytokines and markers, e.g., involved in cell-cell interactions, contribute to the development of therapies for a broad range of degenerative or other conditions which affect the immune system, hematopoietic cells, and other cell types, particularly NK cells. The present invention provides solutions to some of these and many other problems.

SUMMARY OF THE INVENTION

The present invention is based, in part, upon the discovery of a family of cell surface markers. Designated the Kp43 family, these antigens were initially characterized on natural killer (NK) and T cells.

The present invention provides an isolated or recombinant nucleic acid encoding a Kp43 protein; a recombinant or fusion Kp43 protein; or an antibody raised to a recombinant or fusion Kp43 protein.

In an isolated or recombinant nucleic acid embodiments, the nucleic acid has a sequence of SEQ ID NO: 1; encodes an intact extracellular or intact intracellular domain of Kp43; or is in a vector further comprising an origin of replication, a transcription regulatory sequence, or a translation regulatory sequence. Cell transformed with these nucleic acids and animals containing such cells are also encompassed.

In recombinant or fusion Kp43 protein embodiments, typically the protein is isolated, e.g., substantially free of source or naturally accompanying proteins; has an intact extracellular or intracellular domain of Kp43; is a primate protein, including human; has a sequence of SEQ ID NO: 2; or exhibits a post-translational modification pattern distinct from a natural Kp43 protein. In other embodiments, the protein is in a homodimer complex or is admixed with a pharmaceutically acceptable carrier.

In particular antibody embodiments, the Kp43 is from a primate, including human; the antibody is raised against a protein having SEQ ID NO: 2; the antibody is a monoclonal antibody; or the antibody is labeled.

In various kit embodiments, the kit contains an isolated or recombinant nucleic acid encoding a Kp43 protein; a recombinant or fusion Kp43 protein; or an antibody raised to a recombinant or fusion Kp43 protein. In particular embodiments, the isolated or recombinant nucleic acid comprises a sequence of SEQ ID NO: 1; the recombinant or fusion Kp43 protein is a primate protein, including human, has a sequence of SEQ ID NO: 2, or exhibits a post-translational modification pattern distinct from a natural Kp43 protein; or in antibody embodiments, the Kp43 is from a primate, including human, the antibody is raised against a protein having SEQ ID NO: 2, the antibody is a monoclonal antibody; or the antibody is labeled.

The invention also provides methods of screening for a binding partner for Kp43 with steps of producing a recombinant or fusion Kp43 protein; screening a sample for a composition which specifically binds to the Kp43 protein; and selecting that composition.

Also embraced are methods of modulating at least one Kp43-mediated effect on a cell by a Kp43-binding partner by contacting the binding partner with a recombinant or fusion Kp43 protein. For example, the Kp43 protein can exhibit an intact extracellular or intracellular domain of Kp43; the Kp43-mediated effect is IL-2 dependent proliferation, modulation of cytolytic activity, stimulation of activity of phospholipase D; or induction of cytokine biosynthesis; or the cytolytic activity is cell medicated cytotoxicity, or the cytokine biosynthesis is TNF-α biosynthesis.

DETAILED DESCRIPTION OF THE PREFERRED EMBODIMENTS

OUTLINE

I. General
II. Nucleic Acids
  A. natural isolates; methods
  B. synthetic genes
  C. methods to isolate
III. Purified Kp43 protein
  A. physical properties
  B. biological properties
IV. Making Kp43 protein; Mimetics
  A. recombinant methods
  B. synthetic methods
  C. natural purification
V. Physical Variants
  A. sequence variants, fragments
  B. post-translational variants
    1. glycosylation
    2. others
VI. Functional Variants
  A. analogs; fragments
    1. agonists
    2. antagonists
  B. mimetics
    1. protein
    2. chemicals
  C. species variants
VII. Antibodies
  A. polyclonal
  B. monoclonal
  C. fragments, binding compositions
VIII. Uses
  A. diagnostic
  B. therapeutic
IX. Kits
  A. nucleic acid reagents
  B. protein reagents
  C. antibody reagents
X. Methods for Isolating Kp43 Specific Binding Partners

I. General

The present invention provides DNA sequence encoding functionally significant NK and T cell expressed molecules. The cDNA sequence exhibits features characteristic of mRNAs encoding physiologically and developmentally important cell markers. See, e.g., Yokoyama (1993) *Ann. Rev. Immunol.* 11:613–35. The human gene described herein contains an open reading frame encoding a presumptive 179 amino acid protein. The human Kp43 protein described herein represents one member of a class of related genes. Kp43 is a type II integral membrane protein, similar in overall structure to the c-type lectin superfamily. See Drickamer (1993) *Progress in Nucleic Acid Research and Molecular Biology* 45:207.

These proteins are designated Kp43 proteins. The natural proteins should be capable of mediating various physiological responses which would lead to biological responses in target cells. Initial studies had localized this protein to various hematopoietic cell types. See, e.g., Table 1 and Aramburu, et al. (1990) *J. Immunol.* 144:3238–3247. Biochemical properties are described in Table 2.

TABLE 1

Distribution of Kp43 markers.

resting; IL-2 activated NK cells
TCR γ/δ+ T lymphocytes
some TCR α/β+ T lymphocytes
some liver sinusoid cells

TABLE 2

Biochemical Properties of Kp43 markers.

70 kDa disulfide linked dimer
reduced SDS-PAGE mobility of a 43 kDa protein
glycoprotein

II. Nucleic Acids

SEQ ID NO: 1 discloses the nucleotide sequence of one member of the Kp43 family of proteins. The described nucleotide sequence and the related reagents are useful in constructing a DNA clone useful for expressing Kp43 protein, or for isolating or detecting a homologous gene from another natural source, e.g., allelic variants, alternatively spliced isoforms, or counterparts in other species.

The Kp43 described herein has a short cytoplasmic domain of 6 amino acids at the amino terminus. Given that anti-Kp43 monoclonal antibodies induce physiological signals, this implies that there is an association with other signal transducing subunits since it is unlikely that 6 amino acids are sufficient alone for transducing a signal. Between the cytoplasmic domain and the extracellular domain is a typical transmembrane domain, which shows some homology to other similar domains. The extracellular domain has 2 sites for N-linked glycosylation.

Structurally, the Kp43 sequence described herein is remotely similar to NKG2A, with an overall homology of about 32%. This Kp43 exhibits about 30% homology to NKR-P1. This low homology measure suggests that the Kp43 exhibits significant differences from the class of proteins including those proteins.

TABLE 3

Nucleotide sequence encoding a human Kp43 protein and predicted amino acid sequence (SEQ ID NO: 1). Also can use complementary nucleic acid sequences for many purposes.

| TCTAGAGATC | CCTCGACCTC | GAGATCCATT | GTGCTGGAAA | GGCTTCAACA |
|---|---|---|---|---|
| ATTCAACGCT | GTTCTTTCTG | AAAAAGTACA | CATCGTGCCT | TCTCTACTTC |
| GCTCTTGGAA | CATAATTTCT | C | | |

| ATG | GCA | GTG | TTT | AAG | ACC | ACT | CTG | TGG | AGG | TTA | ATT | TCT | GGG | ACC | TTA |
|---|---|---|---|---|---|---|---|---|---|---|---|---|---|---|---|
| GGG | ATA | ATA | TGC | CTT | TCG | TTG | ATG | GCT | ACG | TTG | GGA | ATT | TTG | TTG | AAA |

TABLE 3-continued

Nucleotide sequence encoding a human Kp43 protein and
predicted amino acid sequence (SEQ ID NO: 1). Also can use complementary
nucleic acid sequences for many purposes.

| AAT | TCT | TTT | ACT | AAA | CTG | AGT | ATT | GAG | CCA | GCA | TTT | ACT | CCA | GGA | CCC |
|---|---|---|---|---|---|---|---|---|---|---|---|---|---|---|---|
| AAC | ATA | GAA | CTC | CAG | AAA | GAC | TCT | GAC | TGC | TGT | TCT | TGC | CAA | GAA | AAA |
| TGG | GTT | GGG | TAC | CGG | TGC | AAC | TGT | TAC | TTC | ATT | TCC | AGT | GAA | CAG | AAA |
| ACT | TGG | AAC | GAA | AGT | CGG | CAT | CTC | TGT | GCT | TCT | CAG | AAA | TCC | AGC | CTG |
| CTT | CAG | CTT | CAA | AAC | ACA | GAT | GAA | CTG | GAT | TTT | ATG | AGC | TCC | AGT | CAA |
| CAA | TTT | TAC | TGG | ATT | GGA | CTC | TCT | TAC | AGT | GAG | GAG | CAC | ACC | GCC | TGG |
| TTG | TGG | GAG | AAT | GGC | TCT | GCA | CTC | TCC | CAG | TAT | CTA | TTT | CCA | TCA | TTT |
| GAA | ACT | TTT | AAT | ACA | AAG | AAC | TGC | ATA | GCG | TAT | AAT | CCA | AAT | GGA | AAT |
| GCT | TTA | GAT | GAA | TCC | TGT | GAA | GAT | AAA | AAT | CGT | TAT | ATC | TGT | AAG | CAA |
| CAG | CTC | ATT | TAA | | | | | | | | | | | | |
| ATGTTTCTTG | | GGGCAGAGAA | | GGTGGAGAGT | | AAAGACCCAA | | CATTACTAAC | | | | | | | |
| AATGATACAG | | TTGCATGTTA | | TATTATTACT | | AATTGTCTAC | | TTCTGGAGTC | | | | | | | |
| TATAAAATGT | | TTTTAAACAG | | TGTCATATAC | | AATTGTCATG | | TATGTGAAAC | | | | | | | |
| AATGTGTTTT | | AAAATTGATG | | AAATTCGTTC | | ACCTACATTT | | GAGAATTATA | | | | | | | |
| AAATTAACAT | | | | | | | | | | | | | | | | amino acid sequence (SEQ ID NO: 2)

| MAVFK | TTLWR | LISGT | LGIIC | LSLMA | TLGIL | LKNSF | TKLSI | EPAFT | PGPNI |
|---|---|---|---|---|---|---|---|---|---|
| ELQKD | SDCCS | CQEKW | VGYRC | NCYFI | SSEQK | TWNES | RHLCA | SQKSS | LLQLQ |
| NTDEL | DFMSS | SQQFY | WIGLS | YSEEH | TAWLW | ENGSA | LSQYL | FPSFE | TFNTK |
| NCIAY | NPNGN | ALDES | CEDKN | RYICK | QQLI | | | | |

This invention contemplates use of isolated DNA, including fragments, to encode a biologically active Kp43 protein or polypeptide. In addition, the invention embraces isolated or recombinant DNA capable of hybridizing under appropriate conditions with the DNA sequences described herein, e.g., which encode a biologically active protein. Said biologically active protein or polypeptide can be an intact antigen, or fragment, and have an amino acid sequence as disclosed in SEQ ID NO: 2. Furthermore, this invention covers the use of isolated or recombinant DNA, which includes fragments thereof, which encode proteins which are homologous to a Kp43 protein or which were isolated using cDNA encoding a Kp43 protein as a probe. The isolated DNA can have regulatory sequences in the 5' and 3' flanks, e.g., promoters, enhancers, poly-A addition signals, and others.

An "isolated" nucleic acid is a nucleic acid, e.g., an RNA, DNA, or a mixed polymer, which is substantially separated from other components which naturally accompany a native sequence in its natural environment, e.g., ribosomes, polymerases, and flanking genomic sequences from the original source. The term embraces a nucleic acid sequence which has been removed from its naturally occurring environment, and includes recombinant or cloned DNA isolates and chemically synthesized analogs or analogs biologically synthesized by heterologous systems. The nucleic acid may the entire coding segment, or another partial segment, as described below.

An isolated nucleic acid will generally be a homogeneous composition of molecules, but will, in some embodiments, contain minor heterogeneity. This minor heterogeneity is typically found at the polymer ends or portions not critical to a desired biological function or activity.

A "recombinant" nucleic acid is defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring mutants. Thus, products made by transforming cells with a manipulated vector are encompassed, as are nucleic acids comprising sequence derived using a synthetic oligonucleotide process. Such is often done to replace a codon with a redundant codon encoding the same or a conservative amino acid, while typically introducing or removing a sequence recognition site. Alternatively, it is performed to join nucleic acid segments of desired functions to generate a single genetic entity comprising a desired combination of functions not found in the commonly available natural forms. Restriction enzyme recognition sites are often the target of artificial manipulations, but other site specific targets, e.g., promoters, DNA replication initiation sites, regulation sequences, control sequences, or other useful features may be incorporated by design. A similar concept is intended for a recombinant, e.g., fusion, polypeptide. Specifically included are synthetic nucleic acids which, by genetic code redundancy, encode polypeptides similar to fragments of these antigens, and fusions of sequences from various different species variants.

A significant "fragment" in a nucleic acid context is a contiguous segment of at least about 17 nucleotides, generally at least 20 nucleotides, more generally at least 23 nucleotides, typically at least 29 nucleotides, more typically at least 35 nucleotides, usually at least 45 nucleotides, more usually at least 60 nucleotides, preferably at least 72 nucleotides, more preferably at least 85 nucleotides, and in particularly preferred embodiments will be at least 100 or more nucleotides. The term explicitly is meant to include fragments of the complete coding region, particularly intact structural domains, such as the extracellular or the intracellular fragment.

A DNA which encodes a Kp43 protein will be particularly useful to identify, localize, or quantitate genes, mRNA, and cDNA species which encode related or homologous proteins, as well as DNAs which encode homologous proteins. There are likely homologues in other mammals, e.g., primates. Various Kp43 variant proteins are encompassed herein. However, even proteins that have a more distant evolutionary relationship to the antigen can readily be isolated under appropriate conditions using these sequences if they are sufficiently homologous. Primate Kp43 proteins are of particular interest. Standard hybridization techniques can be applied for isolating genes exhibiting about 70% or better homology.

This invention further covers recombinant DNA molecules and fragments having a DNA sequence identical to or highly homologous to SEQ ID NO: 1, including fragments thereof. In particular, the sequences will often be operably linked to DNA segments which control transcription, translation, and DNA replication. Alternatively, recombinant clones derived from the genomic sequences, e.g., containing introns, will be useful for transgenic studies, including, e.g., transgenic cells and organisms, and for gene therapy. See, e.g., Goodnow (1992) "Transgenic Animals" in Roitt (ed.) *Encyclopedia of Immunology* Academic Press, San Diego, pp. 1502–1504; Travis (1992) *Science* 256:1392–1394; Kuhn, et al. (1991) *Science* 254:707–710; Capecchi (1989) *Science* 244:1288; Robertson (1987)(ed.) *Teratocarcinomas and Embryonic Stem Cells: A Practical Approach* IRL Press, Oxford; Rosenberg (1992) *J. Clinical Oncology* 10:180–199; and Cournoyer, et al. (1993) *Ann. Rev. Immunol.* 11:297–329.

Homologous nucleic acid sequences, when compared, exhibit significant similarity. The standards for homology in nucleic acids are either measures for homology generally used in the art by sequence comparison or based upon hybridization conditions. Hybridization conditions are described in greater detail below.

Substantial homology in the nucleic acid sequence comparison context means either that the segments, or their complementary strands, when compared, are identical when optimally aligned, with appropriate nucleotide insertions or deletions, in at least about 50% of the nucleotides, ordinarily at least 56%, more ordinarily at least 62%, often at least 70%, more often at least about 79%, preferably at least about 88%, more preferably at least about 93% or more, and in particular embodiments, as high at about 97% or more of the nucleotides. Alternatively, substantial homology exists when the segments will hybridize under selective hybridization conditions, to a strand, or its complement, typically using a sequence derived from SEQ ID NO: 1. Selective hybridization will occur when there is at least about 55% homology over a stretch of at least about 14 nucleotides, preferably at least about 65%, more preferably at least about 75%, and most preferably at least about 90%. See, Kanehisa (1984) *Nuc. Acids Res.* 12:203–213. Selectivity usually requires that the number of false positive signals are sufficiently small, e.g., less than a few dozen out of a genome, that hybridization is an effective means to isolate related sequences. The length of homology comparison, as described, may be over longer stretches, and in certain embodiments will be over a stretch of at least about 17 nucleotides, usually at least about 20 nucleotides, more usually at least about 24 nucleotides, typically at least about 28 nucleotides, more typically at least about 40 nucleotides, preferably at least about 50 nucleotides, and more preferably at least about 75 to 100 or more nucleotides.

Stringent conditions, in referring to homology in the hybridization context, will be stringent combined conditions of salt, temperature, organic solvents, and other parameters, typically those controlled in hybridization reactions. Stringent temperature conditions will usually include temperatures in excess of about 30° C., more usually in excess of about 37° C., typically in excess of about 45° C., more typically in excess of about 55° C., preferably in excess of about 65° C., and more preferably in excess of about 70° C. Stringent salt conditions will ordinarily be less than about 800 mM, usually less than about 500 mM, more usually less than about 400 mM, typically less than about 300 mM, preferably less than about 200 mM, and more preferably less than about 150 mM. However, the combination of parameters is much more important than the measure of any single parameter. See, e.g., Wetmur and Davidson (1968) *J. Mol. Biol.* 31:349–370.

III. Purified Kp43 protein

The purified Kp43 protein or defined peptides are useful for generating antibodies by, e.g., standard methods, as described. Synthetic peptides or isolated protein can be presented to an immune system to generate a specific binding composition, e.g., monoclonal or polyclonal antibodies. See, e.g., Coligan (1991) *Current Protocols in Immunology* Wiley/Greene; and Harlow and Lane (1989) *Antibodies: A Laboratory Manual* Cold Spring Harbor Press.

The predicted sequence of human Kp43 amino acid sequence is provided in SEQ ID NO: 2. The peptide sequences allow preparation of peptides to generate antibodies to recognize such segments. As used herein, Kp43 protein shall encompass, when used in a protein context, a protein having amino acid sequences shown in SEQ ID NO: 2, or a significant fragment of such a protein. It also refers to a primate, e.g., human, derived polypeptide which exhibits similar biological function or structural features, e.g., interacts with Kp43' protein specific binding components. These binding components, e.g., antibodies, typically bind to a Kp43 protein with high affinity, e.g., at least about 100 nM, usually better than about 30 nM, preferably better than about 10 nM, and more preferably at better than about 3 nM.

The term polypeptide, as used herein, includes a significant fragment or segment, and encompasses a stretch of amino acid residues of at least about 8 amino acids, generally at least 10 amino acids, more generally at least 13 amino acids, often at least 17 amino acids, more often at least 25 amino acids, preferably at least 35 amino acids, more preferably at least 50 amino acids, and, in particularly preferred embodiments, at least 70 or more amino acids.

An isolated protein typically refers to a protein substantially free from other contaminating proteins, nucleic acids, and other biologicals derived from the native natural source. Purity may be assayed by standard methods, and will ordinarily be at least about 40% pure, more ordinarily at least about 50% pure, typically at least about 60% pure, more typically at least about 75% pure, preferably at least about 85% pure, more preferably at least about 90% pure, and in most preferred embodiments, at least 95% pure. The analysis may be weight or molar percentages, evaluated, e.g., by gel staining, spectrophotometry, or terminus labeling.

Particularly of interest are soluble fragments of Kp43, particularly biologically active fragments. Intact extracellular fragment or intact intracellular fragments will be useful, though intact smaller structural domains are also valuable. Intact exons based upon genomic structure are also of interest.

Solubility of a polypeptide depends upon the environment and the polypeptide. Many parameters affect polypeptide solubility, including temperature, electrolyte environment, size and molecular characteristics of the polypeptide, and nature of the solvent. Typically, the temperature at which the polypeptide is used ranges from about 4° C. to about 65° C. Usually the temperature at use is greater than about 18° C. and more usually greater than about 22° C. For diagnostic purposes, the temperature will usually be about room temperature or warmer, but less than the denaturation temperature of components in the assay. For therapeutic purposes, the temperature will usually be body temperature, typically about 37° C. for humans, though under certain situations the temperature may be raised or lowered in situ or in vitro.

The electrolytes will usually approximate in situ physiological conditions, but may be modified to higher or lower ionic strength where advantageous. The actual ions may be modified, e.g., to conform to standard buffers used in physiological or analytical contexts.

The size and structure of the polypeptide should generally be in a substantially stable state, and usually not in a denatured state. The polypeptide may be associated with other polypeptides in a quaternary structure, e.g., to confer solubility, or associated with lipids or detergents in a manner which approximates natural lipid bilayer interactions.

The solvent will usually be a biologically compatible buffer, of a type used for preservation of biological activities, and will usually approximate a physiological solvent. Usually the solvent will have a neutral pH, typically between about 5 and 10, and preferably about 7.5. On some occasions, a detergent will be added, typically a mild non-denaturing one, e.g., CHS or CHAPS, or a low enough concentration as to avoid significant disruption of structural or physiological properties of the protein.

Solubility is reflected by sedimentation measured in Svedberg units, which are a measure of the sedimentation velocity of a molecule under particular conditions. The determination of the sedimentation velocity was classically performed in an analytical ultracentrifuge, but is typically now performed in a standard ultracentrifuge. See, Freifelder (1982) *Physical Biochemistry* (2d ed.), W. H. Freeman; and Cantor and Schimmel (1980) *Biophysical Chemistry*, parts 1–3, W. H. Freeman & Co., San Francisco. As a crude determination, a sample containing a putatively soluble polypeptide is spun in a standard full sized ultracentrifuge at about 50K rpm for about 10 minutes, and soluble molecules will remain in the supernatant. A soluble particle or polypeptide will typically be less than about 30 S, more typically less than about 15 S, usually less than about 10 S, more usually less than about 6 S, and, in particular embodiments, preferably less than about 4 S, and more preferably less than about 3 S.

Structural features which cause membrane association will often be eliminated. Transmembrane hydrophobic segments or domains which cause membrane linkage are targets for removal to generate soluble Kp43.

IV. Making Kp43 protein; Mimetics

DNA which encodes the Kp43 protein, and including fragments thereof, can be obtained by chemical synthesis, screening cDNA libraries, or by screening genomic libraries prepared from a wide variety of cell lines or tissue samples.

This DNA can be expressed in a wide variety of host cells for the synthesis of protein, full length or fragments, which can in turn, e.g., be used to generate polyclonal or monoclonal antibodies; for binding studies; for construction and expression of modified molecules; and for structure/function studies. Each antigen, complete or fragments, can be expressed in host cells that are transformed or transfected with appropriate expression vectors. These expression products can be substantially purified to be free of protein or cellular contaminants, other than those derived from the recombinant host, and therefore are particularly useful in pharmaceutical compositions when combined with a pharmaceutically acceptable carrier and/or diluent. The antigen may be expressed as fusions with other proteins.

Expression vectors are typically self-replicating DNA or RNA constructs containing the desired antigen gene, usually operably linked to suitable genetic control elements that are recognized in a suitable host cell. These control elements are capable of effecting expression within a suitable host. The specific type of control elements necessary to effect expression will depend upon the eventual host cell used. Generally, the genetic control elements can include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also usually contain an origin of replication that allows the vector to replicate independently of the host cell.

Vectors of this invention contain DNA which encodes a Kp43 protein, including fragments thereof. The DNA can be under the control of a viral promoter and can encode a selection marker. This invention further contemplates use of such expression vectors which are capable of expressing eukaryotic cDNA coding for a Kp43 protein in a prokaryotic or eukaryotic host, where the vector is compatible with the host and where the eukaryotic cDNA coding for the antigen is inserted into the vector such that growth of the host containing the vector expresses the cDNA in question. Usually, expression vectors are designed for stable replication in their host cells or for amplification to greatly increase the total number of copies of the desirable gene per cell. It is not always necessary to require that an expression vector replicate in a host cell, e.g., it is possible to effect transient expression of the antigen, including its fragments, in various hosts using vectors that do not contain a replication origin that is recognized by the host cell. It is also possible to use vectors that cause integration of a Kp43 gene or its fragments into the host DNA by recombination, or to integrate a promoter which controls expression of an endogenous gene.

Vectors, as used herein, encompass plasmids, viruses, bacteriophage, integratable DNA fragments, and other vehicles which enable the integration of DNA fragments into the genome of the host. Expression vectors are specialized vectors which contain genetic control elements that effect expression of operably linked genes. Plasmids are the most commonly used form of vector but other forms of vectors which serve an equivalent function and which are, or become, known in the art are suitable for use herein. See, e.g., Pouwels, et al. (1985 and Supplements) *Cloning Vectors: A Laboratory Manual*, Elsevier, N.Y.; and Rodriquez, et al. (1988)(eds.) *Vectors: A Survey of Molecular Cloning Vectors and Their Uses*, Buttersworth, Boston, MA.

Transformed cells include cells, preferably mammalian, that have been transformed or transfected with vectors containing a Kp43 gene, typically constructed using recombinant DNA techniques. Transformed host cells usually express the antigen or its fragments, but for purposes of cloning, amplifying, and manipulating its DNA, do not need to express the protein. This invention further contemplates culturing transformed cells in a nutrient medium, thus permitting the protein to accumulate in the culture. The protein can be recovered, either from the culture or from the culture medium.

For purposes of this invention, DNA sequences are operably linked when they are functionally related to each other. For example, DNA for a presequence or secretory leader is operably linked to a polypeptide if it is expressed as a preprotein or participates in directing the polypeptide to the cell membrane or in secretion of the polypeptide. A promoter is operably linked to a coding sequence if it controls the transcription of the polypeptide; a ribosome binding site is operably linked to a coding sequence if it is positioned to permit translation. Usually, operably linked means contiguous and in reading frame, however, certain genetic elements such as repressor genes are not contiguously linked but still bind to operator sequences that in turn control expression.

Suitable host cells include prokaryotes, lower eukaryotes, and higher eukaryotes. Prokaryotes include both gram negative and gram positive organisms, e.g., *E. coli* and *B. subtilis*. Lower eukaryotes include yeasts, e.g., *S. cerevisiae* and Pichia, and species of the genus Dictyostelium. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or many of its derivatives. Vectors that can be used to express the Kp43 proteins or its fragments include, but are not limited to, such vectors as those containing the lac promoter (pUC-series); trp promoter (pBR322-trp); Ipp promoter (the pIN-series); lambda-pP or pR promoters (pOTS); or hybrid promoters such as ptac (pDR540). See Brosius, et al. (1988) "Expression Vectors Employing Lambda-, trp-, lac-, and Ipp-derived Promoters", in Rodriguez and Denhardt (eds.) *Vectors: A Survey of Molecular Cloning Vectors and Their Uses*, Buttersworth, Boston, Chapter 10, pp. 205–236.

Lower eukaryotes, e.g., yeasts and Dictyostelium, may be transformed with vectors encoding Kp43 proteins, including fragments. For purposes of this invention, the most common lower eukaryotic host is the baker's yeast, Saccharomyces cerevisiae. It will be used to generically represent lower eukaryotes although a number of other strains and species are also available. Yeast vectors typically consist of a replication origin (unless of the integrating type), a selection gene, a promoter, DNA encoding the desired protein or its fragments, and sequences for translation termination, polyadenylation, and transcription termination. Suitable expression vectors for yeast include such constitutive promoters as 3-phosphoglycerate kinase and various other glycolytic enzyme gene promoters or such inducible promoters as the alcohol dehydrogenase 2 promoter or metallothionine promoter. Suitable vectors include derivatives of the following types: self-replicating low copy number (such as the YRp-series), self-replicating high copy number (such as the YEp-series); integrating types (such as the YIp-series), or mini-chromosomes (such as the YCp-series).

Higher eukaryotic tissue culture cells are the preferred host cells for expression of the functionally active Kp43 protein. In principle, many higher eukaryotic tissue culture cell lines are workable, e.g., insect baculovirus expression systems, whether from an invertebrate or vertebrate source. However, mammalian cells are preferred, in that the processing, both co-translationally and post-translationally should more closely approximate a natural protein. Transformation or transfection and propagation of such cells has become a routine procedure. Examples of useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (if genomic DNA is used), a polyadenylation site, and a transcription termination site. These vectors also usually contain a selection gene or amplification gene. Suitable expression vectors may be plasmids, viruses, or retroviruses carrying promoters derived, e.g., from such sources as from adenovirus, SV40, parvoviruses, vaccinia virus, or cytomegalovirus. Representative examples of suitable expression vectors include pCDNA1; pCD, see Okayama, et al. (1985) *Mol. Cell Biol.* 5:1136–1142; pMC1neo Poly-A, see Thomas, et al. (1987) *Cell* 51:503–512; and a baculovirus vector such as pAC 373 or pAC 610.

It will often be desired to express a Kp43 protein, including a fragment in a system which provides a specific or defined glycosylation pattern. In this case, the usual pattern will be that provided naturally by the expression system. However, the pattern will be modifiable by exposing the polypeptide, e.g., an unglycosylated form, to appropriate glycosylating proteins introduced into a heterologous expression system. For example, the Kp43 protein gene may be co-transformed with one or more genes encoding mammalian or other glycosylating enzymes. Using this approach, certain mammalian glycosylation patterns will be achievable or approximated in prokaryote or other cells.

The Kp43 protein may be engineered to be phosphatidyl inositol (PI) linked to a cell membrane, but can be removed from membranes by treatment with a phosphatidyl inositol cleaving enzyme, e.g., phosphatidyl inositol phospholipase-C. This releases the antigen in a biologically active form, and allows purification by standard procedures of protein chemistry. See, e.g., Low (1989) *Biochim. Biophys. Acta* 988:427–454; Tse, et al. (1985) *Science* 230:1003–1008; and Brunner, et al. (1991) *J. Cell Biol.* 114:1275–1283.

Now that the Kp43 protein has been characterized, fragments or derivatives thereof can be prepared by conventional processes for synthesizing peptides. These include processes such as are described in Stewart and Young (1984) *Solid Phase Peptide Synthesis*, Pierce Chemical Co., Rockford, IL; Bodanszky and Bodanszky (1984) *The Practice of Peptide Synthesis*, Springer-Verlag, New York; and Bodanszky (1984) *The Principles of Peptide Synthesis*, Springer-Verlag, New York. For example, an azide process, an acid chloride process, an acid anhydride process, a mixed anhydride process, an active ester process (for example, p-nitrophenyl ester, N-hydroxysuccinimide ester, or cyanomethyl ester), a carbodiimidazole process, an oxidative-reductive process, or a dicyclohexylcarbodiimide. (DCCD)/ additive process can be used. Solid phase and solution phase syntheses are both applicable to the foregoing processes.

The Kp43 protein, which includes fragments and derivatives, is suitably prepared in accordance with the above processes as typically employed in peptide synthesis, generally either by a so-called stepwise process which comprises condensing an amino acid to the terminal amino acid, one by one in sequence, or by coupling peptide fragments to the terminal amino acid. Amino groups that are not being used in the coupling reaction are typically protected to prevent coupling at an incorrect location.

If a solid phase synthesis is adopted, the C-terminal amino acid is typically bound to an insoluble carrier or support through its carboxyl group. The insoluble carrier usually has a binding capability to a reactive carboxyl group. Examples of such insoluble carriers include halomethyl resins, such as chloromethyl resin or bromomethyl resin, hydroxymethyl resins, phenol resins, tert-alkyloxycarbonyl-hydrazidated resins, and the like.

An amino group-protected amino acid is bound in sequence through condensation of its activated carboxyl group and the reactive amino group of the previously formed peptide or chain, to synthesize the peptide step by step. After synthesizing the desired sequence, the peptide is split off from the insoluble carrier to produce the peptide. This solid-phase approach is generally described by Merrifield, et al. (1963) in *J. Am. Chem. Soc.* 85:2149–2156.

The protein, including fragments thereof, can be isolated and purified from the reaction mixture by means of peptide separation, for example, by extraction, precipitation, electrophoresis and various forms of chromatography, and the like. See, e.g., Deutscher (1990) "Guide to Protein Purification" in *Methods in Enzymology* vol 182, Academic Press. The Kp43 proteins of this invention can be obtained in varying degrees of purity depending upon its desired use. Purification can be accomplished by use of the protein purification techniques disclosed herein or by the use of the antibodies herein described in immunoabsorbant affinity chromatography. This immunoabsorbant affinity chromatography is carried out by first linking the antibodies to a solid support and then contacting the linked antibodies with solubilized lysates of appropriate source cells, lysates of other cells expressing the protein, or lysates or supernatants of cells producing the Kp43 protein as a result of DNA techniques, see below.

V. Physical Variants

This invention also encompasses proteins and peptides having substantial amino acid sequence homology with the amino acid sequence of the Kp43 protein. The variants include species and allelic variants.

Amino acid sequence homology, or sequence identity, is determined by optimizing residue matches, if necessary, by introducing gaps as required. This changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Homologous amino acid sequences are typically intended to include natural allelic and interspecies variations in each respective protein sequence. Typical homologous proteins or peptides will have from 25–100% homology (if gaps can be introduced), to 50–100% homology (if conservative substitutions are included) with the amino acid sequence of the Kp43 protein. Homology measures will be at least about 35%, generally at least 40%, more generally at least 45%, often at least 50%, more often at least 55%, typically at least 60%, more typically at least 65%, usually at least 70%, more usually at least 75%, preferably at least 80%, and more preferably at least 80%, and in particularly preferred embodiments, at least 85% or more. See also Needleham, et al. (1970) *J. Mol. Biol.* 48:443–453; Sankoff, et al. (1983) Chapter One in *Time Warps, String Edits, and Macromolecules: The Theory and Practice of Sequence Comparison* Addison-Wesley, Reading, Mass.; and software packages from IntelliGenetics, Mountain View, Calif.; and the University of Wisconsin Genetics Computer Group, Madison, Wis.

The isolated DNA encoding a Kp43 protein can be readily modified by nucleotide substitutions, nucleotide deletions, nucleotide insertions, and inversions of nucleotide stretches. These modifications result in DNA sequences which encode these antigens, their derivatives, or proteins having similar physiological, immunogenic, or antigenic activity. These modified sequences can be used to produce mutant antigens or to enhance expression. Enhanced expression may involve gene amplification, increased transcription, increased translation, and other mechanisms. Mutant Kp43 protein derivatives include predetermined or site-specific mutations of the respective protein or its fragments. "Mutant Kp43 protein" encompasses a polypeptide otherwise falling within the homology definition of the human Kp43 protein as set forth above, but having an amino acid sequence which differs from that of Kp43 protein as found in nature, whether by way of deletion, substitution, or insertion. In particular, "site specific mutant Kp43 protein" generally includes proteins having significant homology with sequences of SEQ ID NO: 2, and as sharing various biological activities, e.g., antigenic or immunogenic, with those sequences, and in preferred embodiments contain most of the disclosed sequence. Similar concepts apply to different Kp43 proteins, particularly those found in various mammals, e.g., primates, including human. As stated before, it is emphasized that descriptions are generally meant to encompass all Kp43 proteins, including fragments, not limited to the specific embodiment discussed.

Although site specific mutation sites are predetermined, mutants need not be site specific. Kp43 protein mutagenesis can be conducted by making amino acid insertions or deletions. Substitutions, deletions, insertions, or any combinations may be generated to arrive at a final construct. Insertions include amino- or carboxy-terminal fusions. Random mutagenesis can be conducted at a target codon and the expressed mutants can then be screened for the desired activity. Methods for making substitution mutations at predetermined sites in DNA having a known sequence are well known in the art, e.g., by M13 primer mutagenesis or polymerase chain reaction (PCR) techniques. See also Sambrook, et al. (1989) and Ausubel, et al. (1987 and Supplements).

The mutations in the DNA normally should not place coding sequences out of reading frames and preferably will not create complementary regions that could hybridize to produce secondary mRNA structure such as loops or hairpins.

The present invention also provides recombinant proteins, e.g., heterologous fusion proteins using segments from these proteins. A heterologous fusion protein is a fusion of proteins or segments which are naturally not normally fused in the same manner. Thus, the fusion product of an immunoglobulin with a Kp43 polypeptide is a continuous protein molecule having sequences fused in a typical peptide linkage, typically made as a single translation product and exhibiting properties derived from each source peptide. A similar concept applies to heterologous nucleic acid sequences.

In addition, new constructs may be made by combining similar functional domains from other proteins. For example, antigen-binding or other segments may be "swapped" between different new fusion polypeptides or fragments. See, e.g., Cunningham, et al. (1989) *Science* 243:1330–1336; and O'Dowd, et al. (1988) *J. Biol. Chem.* 263:15985–15992. Thus, new chimeric polypeptides exhibiting new combinations of specificities will result from the functional linkage of biologically relevant domains and other functional domains.

The phosphoramidite method described by Beaucage and Carruthers (1981) *Tetra. Letts.* 22:1859–1862, will produce suitable synthetic DNA fragments. See also equipment and manuals for oligonucleotide synthesizers commercially available from Applied Biosystems, Foster City, Calif. A double stranded fragment will often be obtained either by synthesizing the complementary strand and annealing the strand together under appropriate conditions or by adding the complementary strand using DNA polymerase with an appropriate primer sequence, e.g., PCR techniques.

Post-translational variants may also be made by chemical or enzymatic treatment of protein. In particular, glycosylation alterations are included, e.g., made by modifying the glycosylation patterns of a polypeptide during its synthesis and processing, or in further processing steps. Particularly preferred means for accomplishing this are by exposing the polypeptide to glycosylating enzymes derived from cells which normally provide such processing, e.g., mammalian glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine.

VI. Functional Variants

The blocking of physiological response to Kp43 proteins may result from the inhibition of binding of the antigen to its natural binding partner, e.g., through competitive inhibition. Thus, in vitro assays of the present invention will often use isolated protein, membranes from cells expressing a recombinant membrane associated Kp43 protein, soluble fragments comprising binding segments, or fragments attached to solid phase substrates. Preferably, Kp43 will be in a physiologically dimerized structure, of related members of the family, or perhaps homodimers. These assays will also allow for the diagnostic determination of the effects of either binding segment mutations and modifications, or protein mutations and modifications, e.g., analogs.

This invention also contemplates the use of competitive drug screening assays, e.g., where neutralizing antibodies to antigen or binding partner fragments compete with a test compound for binding to the protein. In this manner, the antibodies can be used to detect the presence of any polypeptide which shares one or more antigenic binding sites of the protein and can also be used to occupy binding sites on the protein that might otherwise interact with a binding partner.

Additionally, neutralizing antibodies against the Kp43 protein and soluble fragments of the antigen which contain a high affinity receptor binding site, can be used to inhibit antigen function in tissues, e.g., tissues experiencing abnormal physiology.

"Derivatives" of Kp43 protein include amino acid sequence mutants, glycosylation variants, and covalent or aggregate conjugates with other chemical moieties. Covalent derivatives can be prepared by linkage of functionalities to groups which are found in the Kp43 amino acid side chains or at the N- or C-termini, by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues, e.g., lysine or arginine. Acyl groups are selected from the group of alkyl-moieties including C3 to C18 normal alkyl, thereby forming alkanoyl aroyl species. Covalent attachment to carrier proteins may be important when immunogenic moieties are haptens.

A major group of derivatives are covalent conjugates of the Kp43 protein or fragments thereof with other proteins or polypeptides. These derivatives can be synthesized in recombinant culture such as N- or C-terminal fusions or by the use of agents known in the art for their usefulness in cross-linking proteins through reactive side groups. Preferred antigen derivatization sites with cross-linking agents are at free amino groups, carbohydrate moieties, and cysteine residues.

Fusion polypeptides between the Kp43 proteins and other homologous or heterologous proteins are also provided. Homologous polypeptides may be fusions between different surface markers, resulting in, e.g., a hybrid protein exhibiting receptor binding specificity. Likewise, heterologous fusions may be constructed which would exhibit a combination of properties or activities of the derivative proteins. Typical examples are fusions of a reporter polypeptide, e.g., luciferase, with a segment or domain of an antigen, e.g., a receptor-binding segment, so that the presence or location of the fused antigen may be easily determined. See, e.g., Dull, et al., U.S. Pat. No. 4,859,609, which is hereby incorporated herein by reference. Other gene fusion partners include bacterial β-galactosidase, trpE, Protein A, β-lactamase, alpha amylase, alcohol dehydrogenase, and yeast alpha mating factor. See, e.g., Godowski, et al. (1988) *Science* 241:812–816.

Such polypeptides may also have amino acid residues which have been chemically modified by phosphorylation, sulfonation, biotinylation, or the addition or removal of other moieties, particularly those which have molecular shapes similar to phosphate groups. In some embodiments, the modifications will be useful labeling reagents, or serve as purification targets, e.g., affinity ligands.

Fusion proteins will typically be made by either recombinant nucleic acid methods or by synthetic polypeptide methods. Techniques for nucleic acid manipulation and expression are described generally, for example, in Sambrook, et al. (1989) *Molecular Cloning: A Laboratory Manual* (2d ed.), Vols. 1–3, Cold Spring Harbor Laboratory. Techniques for synthesis of polypeptides are described, for example, in Merrifield (1963) *J. Amer. Chem. Soc.* 85:2149–2156; Merrifield (1986) *Science* 232: 341–347; and Atherton, et al. (1989) *Solid Phase Peptide Synthesis: A Practical Approach*, IRL Press, Oxford.

This invention also contemplates derivatives of the Kp43 proteins other than variations in amino acid sequence or glycosylation. Such derivatives may involve covalent or aggregative association with chemical moieties. These derivatives generally fall into the three classes: (1) salts, (2) side chain and terminal residue covalent modifications, and (3) adsorption complexes, for example with cell membranes. Such covalent or aggregative derivatives are useful as immunogens, as reagents in immunoassays, or in purification methods such as for affinity purification of antigens or other binding proteins. For example, a Kp43 antigen can be immobilized by covalent bonding to a solid support such as cyanogen bromide-activated Sepharose, by methods which are well known in the art, or adsorbed onto polyolefin surfaces, with or without glutaraldehyde cross-linking, for use in the assay or purification of anti-Kp43 protein antibodies or its receptor or other binding partner. The Kp43 antigens can also be labeled with a detectable group, for example radioiodinated by the chloramine T procedure, covalently bound to rare earth chelates, or conjugated to another fluorescent moiety for use in diagnostic assays. Purification of Kp43 protein may be effected by immobilized antibodies or binding partners.

A solubilized Kp43 antigen, including fragment, of this invention can be used as an immunogen for the production of antisera or antibodies specific for the protein or fragments thereof. The purified antigen can be used to screen monoclonal antibodies or binding fragments prepared by immunization with various forms of impure preparations containing the protein. In particular, the term "antibodies" also encompasses antigen binding fragments of natural antibodies. The purified Kp43 proteins can also be used as a reagent to detect any antibodies generated in response to the presence of elevated levels of the protein or cell fragments containing the antigen, both of which may be diagnostic of an abnormal or specific physiological or disease condition. Additionally, antigen fragments may also serve as immunogens to produce the antibodies of the present invention, as described immediately below. For example, this invention contemplates antibodies raised against amino acid sequences encoded by nucleotide sequences shown in Table 1, or fragments of proteins containing them. In particular, this invention contemplates antibodies having binding affinity to or being raised against specific fragments which are predicted to lie outside of the lipid bilayer.

The invention also provides means to isolate a group of related antigens displaying both distinctness and similarities in structure, expression, and function. Elucidation of many of the physiological effects of the antigens will be greatly accelerated by the isolation and characterization of distinct species variants. In particular, the present invention provides useful probes for identifying additional homologous genetic entities in different species.

The isolated genes will allow transformation of cells lacking expression of a corresponding Kp43 protein, e.g., either species types or cells which lack corresponding antigens and should exhibit negative background activity. Expression of transformed genes will allow isolation of antigenically pure cell lines, with defined or single specie variants. This approach will allow for more sensitive detection and discrimination of the physiological effects of Kp43 proteins. Subcellular fragments, e.g., cytoplasts or membrane fragments, can be isolated and used.

Dissection of the critical structural elements which effect various physiological or differentiation functions mediated by the proteins is possible using standard techniques of modern molecular biology, particularly in comparing members of the related family. See, e.g., the homolog-scanning mutagenesis technique described in Cunningham, et al. (1989) *Science* 243:1339–1336; and approaches used in O'Dowd, et al. (1988) *J. Biol. Chem.* 263:15985–15992; and Lechleiter, et al. (1990) *EMBO J.* 9:4381–4390. The invention also provides means, e.g., chemical cross-linking and immunoprecipitation, to isolate other proteins which specifically interact with Kp43.

In particular, functional domains or segments can be substituted between species variants or related proteins to determine what structural features are important in both binding partner affinity and specificity, as well as signal transduction. Cell markers may mediate their effects through interactions involving multiprotein complexes, e.g., Kp43 is found as a dimer. An array of different variants will be useful to screen for molecules exhibiting various combinations of properties, e.g., interaction with different species variants.

Antigen internalization may occur under certain circumstances, allowing interaction between internal cellular components and "normally" extracellular segments of proteins. The specific segments of interaction of Kp43 protein with other intracellular components may be identified by mutagenesis or direct biochemical means, e.g., cross-linking or affinity methods. Structural analysis by crystallographic or other physical methods will also be applicable. Further investigation of the mechanism of biological function will include study of associated components which may be isolatable by affinity methods or by genetic means, e.g., complementation analysis of mutants.

Further study of the expression and control of Kp43 protein will be pursued. The controlling elements associated with the antigens may exhibit differential developmental, tissue specific, or other expression patterns. Upstream or downstream genetic regions, e.g., control elements, are of interest.

Structural studies of the antigen will lead to design of new variants, particularly analogs exhibiting agonist or antagonist properties on binding partners. This can be combined with previously described screening methods to isolate variants exhibiting desired patterns of activities.

Expression in foreign cell types will often result in glycosylation differences in a particular antigen. Various species variants may exhibit distinct functions based upon structural differences. Differential modifications may be responsible for differential function, and elucidation of the effects are now made possible.

Thus, the present invention provides important reagents related to antigen-binding partner interaction. Although the foregoing description has focused primarily upon the human Kp43 protein, those of skill in the art will immediately recognize that the invention encompasses other closely related antigens, e.g., other primate species or allelic variants, as well as variants and other members of the family.

VII. Antibodies

Antibodies can be raised to the various Kp43 proteins, including species or allelic variants, and fragments thereof, both in their isolated forms from natural sources and in their recombinant forms. Additionally, antibodies can be raised to Kp43 proteins in either their active forms or in their inactive forms. Anti-idiotypic antibodies are also contemplated.

Antibodies, including binding fragments and single chain versions, against predetermined fragments of the antigens can be raised by immunization of animals with conjugates of the fragments with immunogenic proteins. Monoclonal antibodies are prepared from cells secreting the desired antibody. These antibodies can be screened for binding to normal or defective Kp43 proteins, or screened for agonistic or antagonistic activity, e.g., mediated through a binding partner. These monoclonal antibodies will usually bind with at least a $K_D$ of about 1 mM, more usually at least about 300 $\mu$M, typically at least about 10 $\mu$M, more typically at least about 30 $\mu$M, preferably at least about 10 $\mu$M, and more preferably at least about 3 $\mu$M or better.

The antibodies, including antigen binding fragments, of this invention can have significant diagnostic or therapeutic value. They can be potent antagonists that bind to a binding partner and inhibit antigen binding or inhibit the ability of an antigen to elicit a biological response. They also can be useful as non-neutralizing antibodies and can be coupled to toxins or radionuclides so that when the antibody binds to the antigen, a cell expressing it, e.g., on its surface, is killed. Further, these antibodies can be conjugated to drugs or other therapeutic agents, either directly or indirectly by means of a linker, and may effect drug targeting.

The antibodies of this invention can also be useful in diagnostic applications. As capture or non-neutralizing antibodies, they can be screened for ability to bind to the antigens without inhibiting binding by a partner. As neutralizing antibodies, they can be useful in competitive binding assays. They will also be useful in detecting or quantifying Kp43 protein or its binding partners. See, e.g., Chan (ed.) (1987) *Immunoassay: A Practical Guide* Academic Press, Orlando, Fla; Price and Newman (eds.)(1991) *Principles and Practice of Immunoassay* Stockton Press, New York; and Ngo (ed.)(1988) *Nonisotopic Immunoassay* Plenum Press, New York.

Antigen fragments may be joined to other materials, particularly polypeptides, as fused or covalently joined polypeptides to be used as immunogens. An antigen and its fragments may be fused or covalently linked to a variety of immunogens, such as keyhole limpet hemocyanin, bovine serum albumin, tetanus toxoid, etc. See *Microbiology*, Hoeber Medical Division, Harper and Row, 1969; Landsteiner (1962) *Specificity of Serological Reactions*, Dover Publications, New York, and Williams, et al. (1967) *Methods in Immunology and Immunochemistry*, Vol. 1, Academic Press, New York, for descriptions of methods of preparing polyclonal antisera. A typical method involves hyperimmunization of an animal with an antigen. The blood of the animal is then collected shortly after the repeated immunizations and gamma globulin is isolated.

In many instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) *Basic and Clinical Immunology* (4th ed.), Lange Medical Publications, Los Altos, Calif., and references cited therein; Harlow and Lane (1988) *Antibodies: A Laboratory Manual*, CSH Press; Goding (1986) *Monoclonal Antibodies: Principles and Practice* (2d ed.) Academic Press, New York; and particularly in Kohler and Milstein (1975) in *Nature* 256: 495–497, which discusses one method of generating monoclonal antibodies. Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secretes a single antibody species to the immunogen. In this manner, the individual antibody species obtained are the products of immortalized and cloned single B cells from the immune animal generated in response to a specific epitope.

Other suitable techniques involve in vitro exposure of lymphocytes to the antigenic polypeptides or alternatively to selection of libraries of antibodies in phage or similar vectors. See, Huse, et al. (1989) "Generation of a Large Combinatorial Library of the Immunoglobulin Repertoire in Phage Lambda," *Science* 246:1275–1281; and Ward, et al. (1989) *Nature* 341:544–546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins and binding fragments may be produced. See Moore, et al. U.S. Pat. No. 4,642,334; and Cabilly, U.S. Pat. No. 4,816,567.

The antibodies of this invention can also be used for affinity chromatography in isolating the protein. Columns can be prepared where the antibodies are linked to a solid support, e.g., particles, such as agarose, Sephadex, or the like, where a cell lysate may be passed through the column, the column washed, followed by increasing concentrations of a mild denaturant, whereby the purified Kp43 protein will be released.

The antibodies may also be used to screen expression libraries for particular expression products. Usually the antibodies used in such a procedure will be labeled with a moiety allowing easy detection of presence of antigen by antibody binding. Similarly, the antibodies may be used for diagnostic detection of Kp43 proteins in a sample, e.g., either qualitative or quantitative immunoassays.

Antibodies raised against each Kp43 protein will also be useful to raise anti-idiotypic antibodies. These will be useful in detecting or diagnosing various immunological conditions related to expression of the respective antigens.

Antibodies are merely one form of specific binding compositions. Other binding compositions, which will often have similar uses, include molecules that bind with specificity to Kp43 protein, e.g., in a binding partner-binding partner fashion, an antibody-antigen interaction, or in a natural physiologically relevant protein-protein interaction, either covalent or non-covalent, e.g., proteins which specifically associate with Kp43 protein. The molecule may be a polymer, or chemical reagent. No implication as to whether Kp43 protein is either the ligand or the receptor of a ligand-receptor interaction is represented, other than the interaction exhibit similar specificity, e.g., specific affinity. A functional analog may be a protein with structural modifications, or may be a structurally unrelated molecule, e.g., which has a molecular shape which interacts with the appropriate binding determinants. The proteins may serve as agonists or antagonists of a binding partner, see, e.g., Goodman, et al. (eds.) (1990) *Goodman & Gilman's: The Pharmacological Bases of Therapeutics* (8th ed.), Pergamon Press.

For example, a specific binding composition could be used for screening an expression library made from a cell line which expresses Kp43 protein. Screening can be standard staining of surface expressed protein, by panning, or other methods. Screening of intracellular expression can also be performed by staining or immunofluorescence procedures. Binding compositions could be used to affinity purify or sort out cells expressing the protein.

VIII. Uses

The present invention provides reagents which will find use in diagnostic applications as described elsewhere herein, e.g., in the general description for physiological or developmental abnormalities, or below in the description of kits for diagnosis.

This invention also provides reagents with significant therapeutic value. The Kp43 protein (naturally occurring or recombinant, and fragments thereof) and antibodies thereto, along with compounds identified as having binding affinity to Kp43 protein, should be useful in the treatment of conditions associated with abnormal physiology or development. In particular, Kp43 has been shown to be involved in proliferation and NK differentiation signals. Abnormal proliferation, degeneration, and under- or over-regulated NK differentiation should be modulatable using the compositions and methods provided herein. In particular, Kp43 may inhibit cell-mediated cytotoxicity, e.g., in transplant rejection or autoimmune reaction situations. For example, a disease or disorder associated with abnormal expression or abnormal signaling by a Kp43 antigen should be a likely target for an agonist or antagonist of the protein.

Other conditions have been attributed to NK cell absence. In particular, certain patients lacking NK cells are susceptible to viral infections. See Biron, et al. (1989) *N.E.J. Medicine* 320:1731–1735. Certain leukemias have also been identified and the patients exhibit anemia and neutropenia. See, e.g., Oshimi (1988) *Leukemia* 2:617–627. These problems may be susceptible to prevention or treatment using compositions provided herein.

Recombinant antibodies which bind to Kp43 can be purified and administered to a patient. These reagents can be combined for therapeutic use with additional active or inert ingredients, e.g., in conventional pharmaceutically acceptable carriers or diluents, e.g., immunogenic adjuvants, along with physiologically innocuous stabilizers and excipients. Combinations of these reagents with other therapeutic medicaments, e.g., those presently used in treating specific ailments, are also made available. These combinations can be sterile filtered and placed into dosage forms as by lyophilization in dosage vials or storage in stabilized aqueous preparations. This invention also contemplates use of antibodies or binding fragments thereof, including forms which are not complement binding.

Screening using Kp43 for binding partners or compounds having binding affinity to Kp43 antigen can be performed, including isolation of associated components. Subsequent biological assays can then be utilized to determine if the compound has intrinsic biological activity and is therefore an agonist or antagonist in that it blocks an activity of the antigen. This invention further contemplates the therapeutic use of antibodies to Kp43 protein as antagonists. This approach should be particularly useful with other Kp43 protein species variants and other members of the family.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds.) (1990) *Goodman and Gilman's: The Pharmacological Bases of Therapeutics*, 8th Ed., Pergamon Press; and *Remington's Pharmaceutical Sciences*, 17th ed. (1990), Mack Publishing Co., Easton, Pa.; each of which is hereby incorporated herein by reference. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index*, Merck & Co., Rahway, N.J. Dosage ranges would ordinarily be expected to be in amounts lower than 1 mM concentrations, typically less than about 10 $\mu$M concentrations, usually less than about 100 nM, preferably less than about 10 pM (picomolar), and most preferably less than about 1 fM (femtomolar), with an appropriate carrier. Slow release formulations, or a slow release apparatus will often be utilized for continuous administration.

Kp43 protein, including fragments thereof, and antibodies to it or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in any conventional dosage formulation. While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds.) (1990) *Goodman and Gilman's: The Pharmacological Bases of Therapeutics*, 8th Ed., Pergamon Press; and *Remington's Pharmaceutical Sciences*, 17th ed. (1990), Mack Publishing Co., Easton, Pa.; Avis, et al. (eds.) (1993) *Pharmaceutical Dosage Forms: Parenteral Medications* Dekker, N.Y.; Lieberman, et al. (eds.) (1990) *Pharmaceutical Dosage Forms: Tablets* Dekker, N.Y.; and Lieberman, et al. (eds.) (1990) *Pharmaceutical Dosage Forms: Disperse Systems* Dekker, N.Y. The therapy of this invention may be combined with or used in association with other chemotherapeutic or chemopreventive agents.

Both the naturally occurring and the recombinant form of the Kp43 proteins of this invention are particularly useful in kits and assay methods which are capable of screening compounds for binding activity to the proteins. Several methods of automating assays have been developed in recent years so as to permit screening of tens of thousands of compounds in a short period. See, e.g., Fodor, et al. (1991) *Science* 251:767–773, which is incorporated herein by reference and which describes means for testing of binding affinity by a plurality of defined polymers synthesized on a solid substrate. The development of suitable assays can be greatly facilitated by the availability of large amounts of purified, soluble Kp43 protein as provided by this invention.

This invention is particularly useful for screening compounds by using recombinant antigen in any of a variety of drug screening techniques. The advantages of using a recombinant protein in screening for specific ligands include: (a) improved renewable source of the antigen from a specific source; (b) potentially greater number of antigen molecules per cell giving better signal to noise ratio in assays; and (c) species variant specificity (theoretically giving greater biological and disease specificity). The purified protein may be tested in numerous assays, typically in vitro assays, which evaluate biologically relevant responses. See, e.g., Coligan *Current Protocols in Immunology*; Hood, et al. *Immunology* Benjamin/Cummings; Paul (ed.) *Fundamental Immunology*; and *Methods in Enzymology* Academic Press. This will also be useful in screening for a ligand which binds a Kp43, e.g., from cells known to interact with Kp43 containing cells.

One method of drug screening utilizes eukaryotic or prokaryotic host cells which are stably transformed with recombinant DNA molecules expressing the Kp43 antigens. Cells may be isolated which express an antigen in isolation from other functionally equivalent antigens. Such cells, either in viable or fixed form, can be used for standard protein-protein binding assays. See also, Parce, et al. (1989) *Science* 246:243–247; and Owicki, et al. (1990) *Proc. Nat'l Acad. Sci. USA* 87:4007–4011, which are incorporated herein by reference and describe sensitive methods to detect cellular responses. Competitive assays are particularly useful, where the cells (source of Kp43 protein) are contacted and incubated with a labeled binding partner or antibody having known binding affinity to Kp43, such as $^{125}$I-antibody, and a test sample whose binding affinity to the binding composition is being measured. The bound and free labeled binding compositions are then separated to assess the degree of antigen binding. The amount of test compound bound is inversely proportional to the amount of labeled antibody binding to the known source. Any one of numerous techniques can be used to separate bound from free protein to assess the degree of binding. This separation step could typically involve a procedure such as adhesion to filters followed by washing, adhesion to plastic followed by washing, or centrifugation of the cell membranes. Viable cells could also be used to screen for the effects of drugs on Kp43 protein mediated functions, e.g., cell proliferation, i.e., IL-2 dependent; cytotoxic activity, i.e., cell-mediated; phospholipase D activity; cytokine biosynthesis, e.g., TNF-α; and others. Some detection methods allow for elimination of a separation step, e.g., a proximity sensitive detection system. Calcium sensitive dyes will be useful for detecting $Ca^{++}$ levels, with a fluorimeter or a fluorescence cell sorting apparatus.

Another method utilizes membranes from transformed eukaryotic or prokaryotic host cells as the source of the Kp43 protein. These cells are stably transformed with DNA vectors directing the expression of a membrane associated Kp43 protein. Essentially, the membranes would be prepared from the cells and used in any marker-marker type binding assay such as the competitive assay set forth above.

Still another approach is to use solubilized, unpurified or solubilized, purified Kp43 protein from transformed eukaryotic or prokaryotic host cells. This allows for a "molecular" binding assay with the advantages of increased specificity, the ability to automate, and high drug test throughput.

Another technique for drug screening involves an approach which provides high throughput screening for compounds having suitable binding affinity to Kp43 and is described in detail in Geysen, European Patent Application 84/03564, published on Sep. 13, 1984. First, large numbers of different small peptide test compounds are synthesized on a solid substrate, e.g., plastic pins or some other appropriate surface, see Fodor, et al. (1991). Then all the pins are reacted with solubilized, unpurified or solubilized, purified Kp43 binding composition, and washed. The next step involves detecting bound binding composition.

Rational drug design may also be based upon structural studies of the molecular shapes of the Kp43 protein and other effectors or analogs. Effectors may be other proteins which mediate other functions in response to antigen binding, or other proteins which normally interact with the antigen, e.g., Kp43 ligand. One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) *Protein Crystalloaraphy*, Academic Press, New York.

Purified Kp43 protein can be coated directly onto plates for use in the aforementioned drug screening techniques. However, non-neutralizing antibodies to Kp43 can be used as capture antibodies to immobilize protein on the solid phase.

IX. Kits

This invention also contemplates use of Kp43 proteins, including fragments thereof, peptides, and their fusion products in a variety of diagnostic kits and methods for detecting the presence of a binding composition. Typically the kit will have a compartment containing either a defined Kp43 protein or gene segment or a reagent which recognizes one or the other, e.g., Kp43 fragments or antibodies. See, e.g., Chan (ed.)(1987) *Immunoassay: A Practical Guide* Academic Press, Orlando, Fla.; Price and Newman (eds.)(1991) *Principles and Practice of Immunoassay* Stockton Press, NY; and Ngo (ed.)(1988) *Nonisotopic Immunoassay* Plenum Press, N.Y.

A kit for determining the binding affinity of a test compound to a Kp43 protein would typically comprise a test compound; a labeled compound, for example an antibody having known binding affinity for the protein; a source of Kp43 protein (naturally occurring or recombinant); and a means for separating bound from free labeled compound, such as a solid phase for immobilizing the protein. Once compounds are screened, those having suitable binding affinity to the antigen can be evaluated in suitable biological assays, as are well known in the art, to determine whether they exhibit similar biological activities to the natural protein. The availability of recombinant Kp43 protein also provides well defined standards for calibrating such assays.

A preferred kit for determining the concentration of, for example, a Kp43 protein in a sample would typically comprise a labeled compound, e.g., antibody, having known binding affinity, a source of antigen (naturally occurring or recombinant) and a means for separating the bound from free labeled compound, for example, a solid phase for immobilizing the Kp43 protein. Compartments containing reagents, and instructions, will normally be provided.

One method for determining the concentration of Kp43 protein in a sample would typically comprise the steps of: (1) preparing membranes from a sample comprised of a membrane bound Kp43 protein source; (2) washing the membranes and suspending them in a buffer; (3) solubilizing the antigen by incubating the membranes in a culture medium to which a suitable detergent has been added; (4) adjusting the detergent concentration of the solubilized antigen; (5) contacting and incubating said dilution with radiolabeled antibody to form complexes; (6) recovering the complexes such as by filtration through polyethyleneimine treated filters; and (7) measuring the radioactivity of the recovered complexes.

Antibodies, including antigen binding fragments, specific for the Kp43 protein are useful in diagnostic applications to detect the presence of elevated levels of Kp43 protein and/or its fragments. Such diagnostic assays can employ lysates, live cells, fixed cells, immunofluorescence, cell cultures, body fluids, and further can involve the detection of antigens related to the protein in serum, or the like. Diagnostic assays may be homogeneous (without a separation step between free reagent and protein-protein complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA), and the like. For example, unlabeled antibodies can be employed by using a second antibody which is labeled and which recognizes the antibody to a Kp43 protein or to a particular fragment thereof. Similar assays have also been extensively discussed in the literature. See, e.g., Harlow and Lane (1988) *Antibodies: A Laboratory Manual*, CSH.

Anti-idiotypic antibodies may have similar use to diagnose presence of antibodies against a Kp43 protein, as such may be diagnostic of various abnormal states. For example, overproduction of Kp43 protein may cause various immunological reactions which may be diagnostic of abnormal physiological states, particularly in proliferative cell conditions such as cancer or abnormal differentiation.

Frequently, reagents for diagnostic assays are supplied in kits, so as to optimize the sensitivity of the assay. For the subject invention, depending upon the nature of the assay, the protocol, and the label, either labeled or unlabeled antibody, or labeled Kp43 protein is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium providing appropriate concentrations of reagents for performing the assay.

Any of the aforementioned constituents of the drug screening and the diagnostic assays may be used without modification or may be modified in a variety of ways. For example, labeling may be achieved by covalently or non-covalently joining a moiety which directly or indirectly provides a detectable signal. In any of these assays, the antigen, test compound, Kp43 protein, or antibodies thereto can be labeled either directly or indirectly. Possibilities for direct labeling include label groups: radiolabels such as $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups.

There are also numerous methods of separating the bound from the free antigen, or alternatively the bound from the free test compound. The Kp43 protein can be immobilized on various matrixes followed by washing. Suitable matrixes include plastic such as an ELISA plate, filters, and beads. Methods of immobilizing the Kp43 protein to a matrix include, without limitation, direct adhesion to plastic, use of a capture antibody, chemical coupling, and biotin-avidin. The last step in this approach involves the precipitation of protein-protein complex by any of several methods including those utilizing, e.g., an organic solvent such as polyethylene glycol or a salt such as ammonium sulfate. Other suitable separation techniques include, without limitation, the fluorescein antibody magnetizable particle method described in Rattle, et al. (1984) *Clin. Chem.* 30:1457–1461, and the double antibody magnetic particle separation as described in U.S. Pat. No. 4,659,678.

The methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of a Kp43 protein. These sequences can be used as probes for detecting levels of antigen message in samples from patients suspected of having an abnormal condition, e.g., cancer or developmental problem. The preparation of both RNA and DNA nucleotide sequences, the labeling of the sequences, and the preferred size of the sequences has received ample description and discussion in the literature. Normally an oligonucleotide probe should have at least about 14 nucleotides, usually at least about 18 nucleotides, and the polynucleotide probes may be up to several kilobases. Various labels may be employed, most commonly radionuclides, particularly $^{32}$P. However, other techniques may also be employed, such as using biotin modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed which can recognize specific duplexes, including DNA duplexes, RNA duplexes, DNA-RNA hybrid duplexes, or DNA-protein duplexes. The antibodies in turn may be labeled and the assay carried out where the duplex is bound to a surface, so that upon the formation of duplex on the surface, the presence of antibody bound to the duplex can be detected. The use of probes to the novel anti-sense RNA may be carried out in any conventional techniques such as nucleic acid hybridization, plus and minus screening, recombinational probing, hybrid released translation (HRT), and hybrid arrested translation (HART). This also includes amplification techniques such as polymerase chain reaction (PCR).

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet, et al. (1989) *Progress in Growth Factor Res.* 1:89–97.

x. Methods for Isolating Kp43 Specific Binding Partners

The Kp43 protein should interact with a binding counter-partner based, e.g., upon its similarity in structure and function to other cell markers exhibiting developmental and cell type specificity of expression. Methods to isolate a binding partner, e.g., on the surface of another cell, are made available by the ability to make purified Kp43 for screening programs. Soluble or other constructs using the Kp43 sequences provided herein will allow for screening or isolation of Kp43 specific ligands, e.g., using screening methods as described, including sorting, panning, and specific labeling.

Intracellular proteins which associate with the intracellular domain of the described Kp43 should also be isolatable by similar methods, including affinity labeling or purification or chemical cross-linking.

The broad scope of this invention is best understood with reference to the following examples, which are not intended to limit the invention to specific embodiments.

EXAMPLES

I. General Methods

Some of the standard methods are described or referenced, e.g., in Maniatis, et al. (1982) *Molecular Cloning, A Laboratory Manual*, Cold Spring Harbor Laboratory, Cold Spring Harbor Press; Sambrook, et al. (1989) *Molecular Cloning: A Laboratory Manual*; (2d ed.), vols 1–3, CSH Press, N.Y; Ausubel, et al., *Biology*, Greene Publishing Associates, Brooklyn, N.Y.; or Ausubel, et al. (1987 and Supplements) *Current Protocols in Molecular Biology*, Greene/Wiley, N.Y.; Innis, et al. (eds.)(1990) *PCR Protocols: A Guide to Methods and Applications* Academic Press, N.Y.; all of which are each incorporated herein by reference. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification" in *Methods in Enzymology*, vol. 182, and other volumes in this series; and manufacturer's literature on use of protein purification products, e.g., Pharmacia, Piscataway, N.J., or Bio-Rad, Richmond, Calif.; which are incorporated herein by reference. Combination with recombinant techniques allow fusion to appropriate segments, e.g., to a FLAG sequence or an equivalent which can be fused via a protease-removable sequence. See, e.g., Hochuli (1989) *Chemische Industrie* 12:69–70; Hochuli (1990) "Purification of Recombinant Proteins with Metal Chelate Absorbent" in Setlow (ed.) *Genetic Engineering, Principle and Methods* 12:87–98, Plenum Press, N.Y.; and Crowe, et al. (1992) *OIAexpress: The High Level Expression & Protein Purification System* QUIAGEN, Inc., Chatsworth, Calif.; which are incorporated herein by reference.

FACS analyses are described in Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y.

II. Preparation of a Monoclonal antibody.

Preparation of the HP3B1 monoclonal antibody which recognizes the Kp43 antigen is described in Aramburu, et al. (1990) *J. Immunol.* 144:3238–3247. Briefly, Balb/c mice were immunized with cultured NK cells. Splenocytes were fused with a P3X63/Ag.8.653 mouse myeloma cells and hybridomas were selected for production of an antibody which (1) inhibits IL-2 induced proliferation of NK cells, and (2) binds to NK cells and PBL by indirect immunofluorescence.

III. Distribution of Kp43 Antigen.

Kp43 antigen is expressed on specific populations of human peripheral blood NK cells. See Table 1. Distribution studies may be performed by standard histological procedures or by labeling and cell sorting, where cell types are dispersed.

IV. Biochemical Characterization of Kp43.

Anti-Kp43 antibody recognizes a disulfide-linked homodimer glycoprotein (MW ~70 kD non-reducing; ~43 kD reducing) on human T cells and NK cells, based on 2 dimensional (non-reduced/reduced) SDS-PAGE analysis. See Table 2. In theory, it is possible that disulfide-linked heterodimers may exist between different Kp43 family members.

V. Isolation of a DNA clone encoding Kp43 protein.

Kp43 antigen was expression cloned from a polyclonal human activated NK cell cDNA library in the pJFE14 expression vector. COS7 cells were transfected with the library and antigen positive cells were selected using phycoerythrin labeled anti-Kp43 mAb. A clone LL288 was isolated. The cDNA sequence revealed a type II membrane protein with a predicted MW of about 21 kD with 2 N-linked glycosylation sites, consistent with the expected size based on prior biochemical analysis.

In another method, oligonucleotides based upon SEQ ID NO 1 are used to screen a library. In combination with polymerase chain reaction (PCR) techniques, synthetic oligonucleotides in appropriate orientations are used as primers to select correct clones from a library.

Biochemical Characterization of the Kp43 protein.

A recombinant Kp43 construct is prepared which is fused to a useful affinity reagent, e.g., FLAG peptide, useful for purifying the expression product of the construct. See, e.g., Crowe, et al. (1992) *OIAexpress: The High Level Expression & Protein Purification System* QUIAGEN, Inc. Chatsworth, Calif.; and Hopp, et al. (1988) *Bio/Technology* 6:1204–1210. The sequence allows for efficient affinity purification of the soluble product. Appropriate secretion or processing sites may also be engineered into the construct by standard methods. Purification is achieved by use of affinity purification, e.g., antibodies against the antigen, or by standard protein purification methods. Typically, the affinity reagents or purification procedures can be performed on recombinant protein.

Preparation of antibodies specific for Kp43

Synthetic peptides or purified protein are presented to an immune system to generate monoclonal or polyclonal antibodies. See, e.g., Coligan (1991) *Current Protocols in Immunology* Wiley/Greene; and Harlow and Lane (1989) *Antibodies: A Laboratory Manual* Cold Spring Harbor Press. In appropriate situations, the binding reagent is either labeled as described above, e.g., fluorescence or otherwise, or immobilized to a substrate for panning methods.

Purification of the Kp43 protein

The Kp43 protein is isolated by a combination of affinity chromatography using Kp43 specific binding compositions, e.g., antibody, as a specific binding reagent in combination with protein purification techniques allowing separation from other proteins and contaminants. Similar techniques using other species' cell assays and cell sources are applied to isolate corresponding antigens from other species.

All references cited herein are incorporated herein by reference to the same extent as if each individual publication or patent application was specifically and individually indicated to be incorporated by reference.

Applicants have deposited a culture of *E. coli* carrying a plasmid with the LL288 cDNA insert, whose sequence is provided in Table 3, with the American Type Culture Collection, Rockville, Md., USA (ATCC) under accession number 69498.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. An isolated or recombinant nucleic acid encoding at least a 13 amino acid antigenic fragment of a Kp43 protein having the sequence of SEQ ID NO: 2.

2. The recombinant nucleic acid of claim 1, wherein said nucleic acid encodes the extracellular portion of the Kp43 having the sequence of SEQ ID NO: 2.

3. A host cell transformed with a nucleic acid of claim 2.

4. The nucleic acid of claim 1 in a vector further comprising an origin of replication, a transcription regulatory sequence, or a translation regulatory sequence.

5. A cell transformed with a nucleic acid of claim 4.

6. The nucleic acid of claim 1, which encodes a full length Kp43 protein having the sequence of SEQ ID NO: 2.

7. A host cell transformed with a nucleic acid of claim 6.

8. The nucleic acid of claim 1 that has the sequence of SEQ ID NO: 1.

9. The nucleic acid of claim 1 that encodes at least a 17 amino acid antigenic fragment of a Kp43 protein having the sequence of SEQ ID NO: 2.

10. The nucleic acid of claim 9 that encodes at least a 25 amino acid antigenic fragment of a Kp43 protein having the sequence of SEQ ID NO: 2.

11. The nucleic acid of claim 10 that encodes at least a 50 amino acid antigenic fragment of a Kp43 protein having the sequence of SEQ ID NO: 2.

12. The nucleic acid of claim 11 that encodes at least a 70 amino acid antigenic fragment of a Kp43 protein having the sequence of SEQ ID NO: 2.

13. The nucleic acid of claim 10 that has the sequence of SEQ ID NO: 1.

14. An isolated or recombinant nucleic acid encoding at least a 13 amino acid antigenic fragment of a Kp43 protein having the sequence of SEQ ID NO: 2, wherein said nucleic acid comprises a sequence of nucleotides 122 to 658 from SEQ ID NO: 1.

15. An isolated or recombinant nucleic acid encoding a full-length Kp43 protein, wherein said Kp43 protein is a natural allelic variant of the Kp43 protein having the sequence of SEQ ID NO: 2.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:

(A) LENGTH: 871 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 122..661

(xi) SEQUENCE DESCRIPTION: SEQ ID NO:1:

```
TCTAGAGATC  CCTCGACCTC  GAGATCCATT  GTGCTGGAAA  GGCTTCAACA  ATTCAACGCT      60

GTTCTTTCTG  AAAAAGTACA  CATCGTGCCT  TCTCTACTTC  GCTCTTGGAA  CATAATTTCT     120

C  ATG  GCA  GTG  TTT  AAG  ACC  ACT  CTG  TGG  AGG  TTA  ATT  TCT  GGG  ACC     166
   Met  Ala  Val  Phe  Lys  Thr  Thr  Leu  Trp  Arg  Leu  Ile  Ser  Gly  Thr
   1                5                      10                     15

TTA  GGG  ATA  ATA  TGC  CTT  TCG  TTG  ATG  GCT  ACG  TTG  GGA  ATT  TTG  TTG    214
Leu  Gly  Ile  Ile  Cys  Leu  Ser  Leu  Met  Ala  Thr  Leu  Gly  Ile  Leu  Leu
              20                      25                           30

AAA  AAT  TCT  TTT  ACT  AAA  CTG  AGT  ATT  GAG  CCA  GCA  TTT  ACT  CCA  GGA    262
Lys  Asn  Ser  Phe  Thr  Lys  Leu  Ser  Ile  Glu  Pro  Ala  Phe  Thr  Pro  Gly
              35                      40                      45

CCC  AAC  ATA  GAA  CTC  CAG  AAA  GAC  TCT  GAC  TGC  TGT  TCT  TGC  CAA  GAA    310
Pro  Asn  Ile  Glu  Leu  Gln  Lys  Asp  Ser  Asp  Cys  Cys  Ser  Cys  Gln  Glu
              50                      55                      60

AAA  TGG  GTT  GGG  TAC  CGG  TGC  AAC  TGT  TAC  TTC  ATT  TCC  AGT  GAA  CAG    358
Lys  Trp  Val  Gly  Tyr  Arg  Cys  Asn  Cys  Tyr  Phe  Ile  Ser  Ser  Glu  Gln
     65                      70                      75

AAA  ACT  TGG  AAC  GAA  AGT  CGG  CAT  CTC  TGT  GCT  TCT  CAG  AAA  TCC  AGC    406
Lys  Thr  Trp  Asn  Glu  Ser  Arg  His  Leu  Cys  Ala  Ser  Gln  Lys  Ser  Ser
80                      85                      90                      95

CTG  CTT  CAG  CTT  CAA  AAC  ACA  GAT  GAA  CTG  GAT  TTT  ATG  AGC  TCC  AGT    454
Leu  Leu  Gln  Leu  Gln  Asn  Thr  Asp  Glu  Leu  Asp  Phe  Met  Ser  Ser  Ser
                    100                     105                     110

CAA  CAA  TTT  TAC  TGG  ATT  GGA  CTC  TCT  TAC  AGT  GAG  GAG  CAC  ACC  GCC    502
Gln  Gln  Phe  Tyr  Trp  Ile  Gly  Leu  Ser  Tyr  Ser  Glu  Glu  His  Thr  Ala
               115                     120                     125

TGG  TTG  TGG  GAG  AAT  GGC  TCT  GCA  CTC  TCC  CAG  TAT  CTA  TTT  CCA  TCA    550
Trp  Leu  Trp  Glu  Asn  Gly  Ser  Ala  Leu  Ser  Gln  Tyr  Leu  Phe  Pro  Ser
          130                     135                     140

TTT  GAA  ACT  TTT  AAT  ACA  AAG  AAC  TGC  ATA  GCG  TAT  AAT  CCA  AAT  GGA    598
Phe  Glu  Thr  Phe  Asn  Thr  Lys  Asn  Cys  Ile  Ala  Tyr  Asn  Pro  Asn  Gly
     145                     150                     155

AAT  GCT  TTA  GAT  GAA  TCC  TGT  GAA  GAT  AAA  AAT  CGT  TAT  ATC  TGT  AAG    646
Asn  Ala  Leu  Asp  Glu  Ser  Cys  Glu  Asp  Lys  Asn  Arg  Tyr  Ile  Cys  Lys
160                     165                     170                     175

CAA  CAG  CTC  ATT  TAAATGTTTC  TTGGGGCAGA  GAAGGTGGAG  AGTAAAGACC              698
Gln  Gln  Leu  Ile
               180

CAACATTACT  AACAATGATA  CAGTTGCATG  TTATATTATT  ACTAATTGTC  TACTTCTGGA     758

GTCTATAAAA  TGTTTTTAAA  CAGTGTCATA  TACAATTGTC  ATGTATGTGA  AACAATGTGT     818

TTTAAAATTG  ATGAAATTCG  TTCACCTACA  TTTGAGAATT  ATAAAATTAA  CAT            871
```

(2) INFORMATION FOR SEQ ID NO:2:

(i) SEQUENCE CHARACTERISTICS:
(A) LENGTH: 179 amino acids
(B) TYPE: amino acid
(D) TOPOLOGY: linear (ii) MOLECULE TYPE: protein (xi) SEQUENCE DESCRIPTION: SEQ ID NO:2:

```
Met Ala Val Phe Lys Thr Thr Leu Trp Arg Leu Ile Ser Gly Thr Leu
 1               5                   10                  15
Gly Ile Ile Cys Leu Ser Leu Met Ala Thr Leu Gly Ile Leu Leu Lys
            20                  25                  30
Asn Ser Phe Thr Lys Leu Ser Ile Glu Pro Ala Phe Thr Pro Gly Pro
        35                  40                  45
Asn Ile Glu Leu Gln Lys Asp Ser Asp Cys Cys Ser Cys Gln Glu Lys
    50                  55                  60
Trp Val Gly Tyr Arg Cys Asn Cys Tyr Phe Ile Ser Ser Glu Gln Lys
65                  70                  75                  80
Thr Trp Asn Glu Ser Arg His Leu Cys Ala Ser Gln Lys Ser Ser Leu
                85                  90                  95
Leu Gln Leu Gln Asn Thr Asp Glu Leu Asp Phe Met Ser Ser Ser Gln
            100                 105                 110
Gln Phe Tyr Trp Ile Gly Leu Ser Tyr Ser Glu Glu His Thr Ala Trp
        115                 120                 125
Leu Trp Glu Asn Gly Ser Ala Leu Ser Gln Tyr Leu Phe Pro Ser Phe
    130                 135                 140
Glu Thr Phe Asn Thr Lys Asn Cys Ile Ala Tyr Asn Pro Asn Gly Asn
145                 150                 155                 160
Ala Leu Asp Glu Ser Cys Glu Asp Lys Asn Arg Tyr Ile Cys Lys Gln
                165                 170                 175
Gln Leu Ile
```